US007867219B2

(12) United States Patent
Chambers

(10) Patent No.: US 7,867,219 B2
(45) Date of Patent: Jan. 11, 2011

(54) CATHETER WITH FLEXIBLE TIP AND SHAPE RETENTION

(75) Inventor: Jeffrey W. Chambers, Plymouth, MN (US)

(73) Assignee: Chambers Technologies, LLC, Mackinac Island, MI (US)

( * ) Notice: Subject to any disclaimer, the term of this patent is extended or adjusted under 35 U.S.C. 154(b) by 824 days.

(21) Appl. No.: 11/542,345

(22) Filed: Oct. 3, 2006

(65) Prior Publication Data
US 2007/0049899 A1 Mar. 1, 2007

Related U.S. Application Data

(63) Continuation of application No. 10/064,498, filed on Jul. 22, 2002, now Pat. No. 7,115,134.

(51) Int. Cl.
*A61M 25/00* (2006.01)
(52) U.S. Cl. .................. 604/532; 604/508; 604/528
(58) Field of Classification Search ............ 604/527, 604/525
See application file for complete search history.

(56) References Cited

U.S. PATENT DOCUMENTS 4,920,980 A * 5/1990 Jackowski .............. 607/123
5,718,680 A * 2/1998 Kraus et al. ............... 604/509
5,857,997 A * 1/1999 Cimino et al. ........... 604/95.01
6,086,548 A * 7/2000 Chaisson et al. ............ 600/585
6,199,262 B1 * 3/2001 Martin .................... 29/525.15
6,350,253 B1 * 2/2002 Deniega et al. ......... 604/164.02
6,652,472 B2 * 11/2003 Jafari et al. ................ 600/585

* cited by examiner

Primary Examiner—Nicholas D Lucchesi
Assistant Examiner—Pritesh Patel
(74) Attorney, Agent, or Firm—Dicke, Billig & Czaja, PLLC

(57) ABSTRACT

An improved apparatus and method to catheterize passages is disclosed. The present invention provides a catheter having a soft flexible pre-formed distal tip, that when used in combination with commercially available guidewires of variable stiffness, results in the ability to control the direction and angle of wire advancement allowing cannulation of body passages, including those that arise at acute angles. The catheter can have a longitudinal axis, a proximal section and a distal section having a soft flexible pre-formed tip having a curvature of ninety degrees or greater and shape retention. The catheter can have an inner wall that defines a lumen that runs along said longitudinal axis forming a single continuous tube, a reinforcement braid disposed over the inner wall, and an outside covering disposed over the reinforcement braid. A spacer can be added between said wall liner and said reinforcement braid in the proximal end.

9 Claims, 15 Drawing Sheets

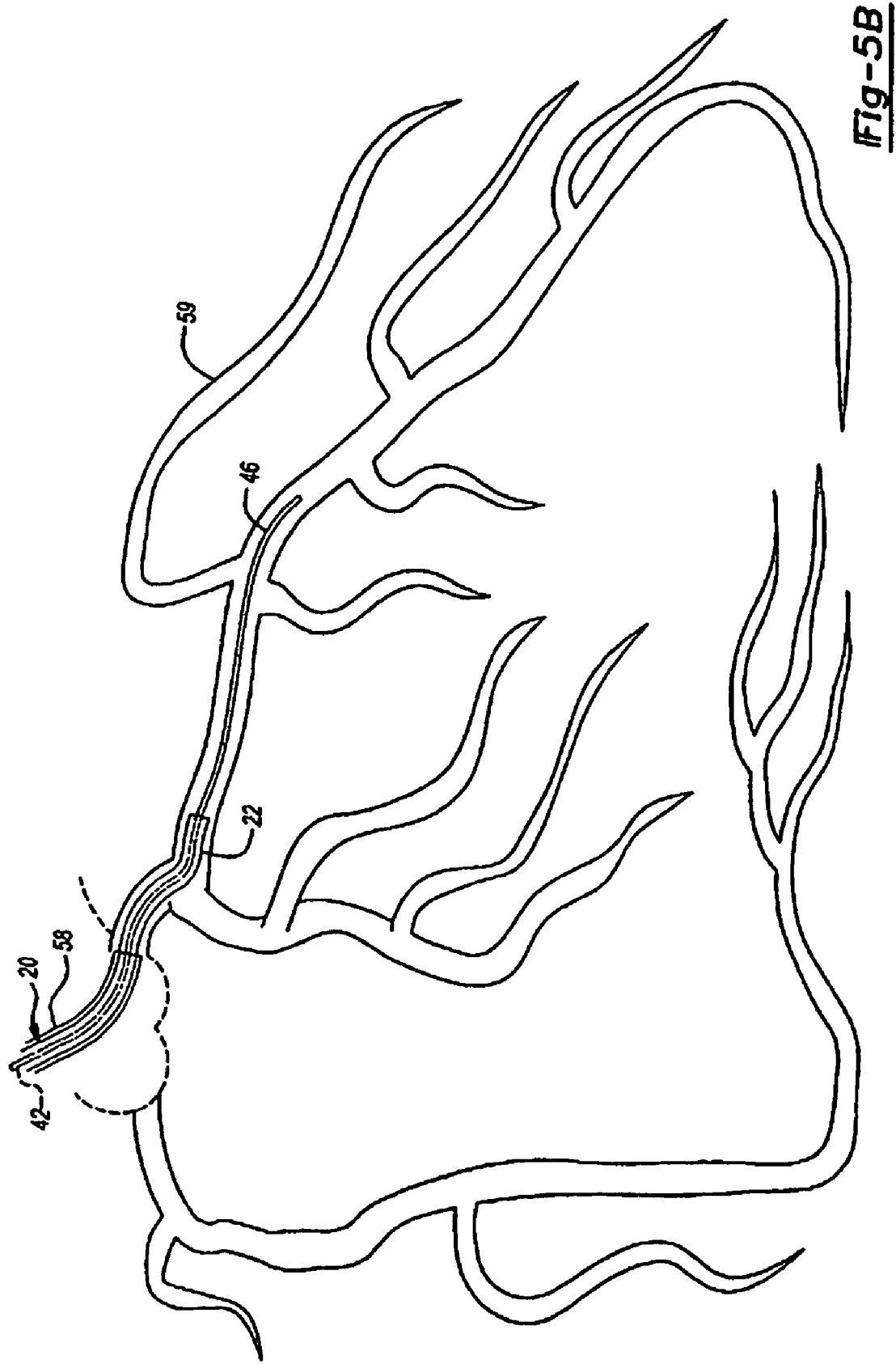

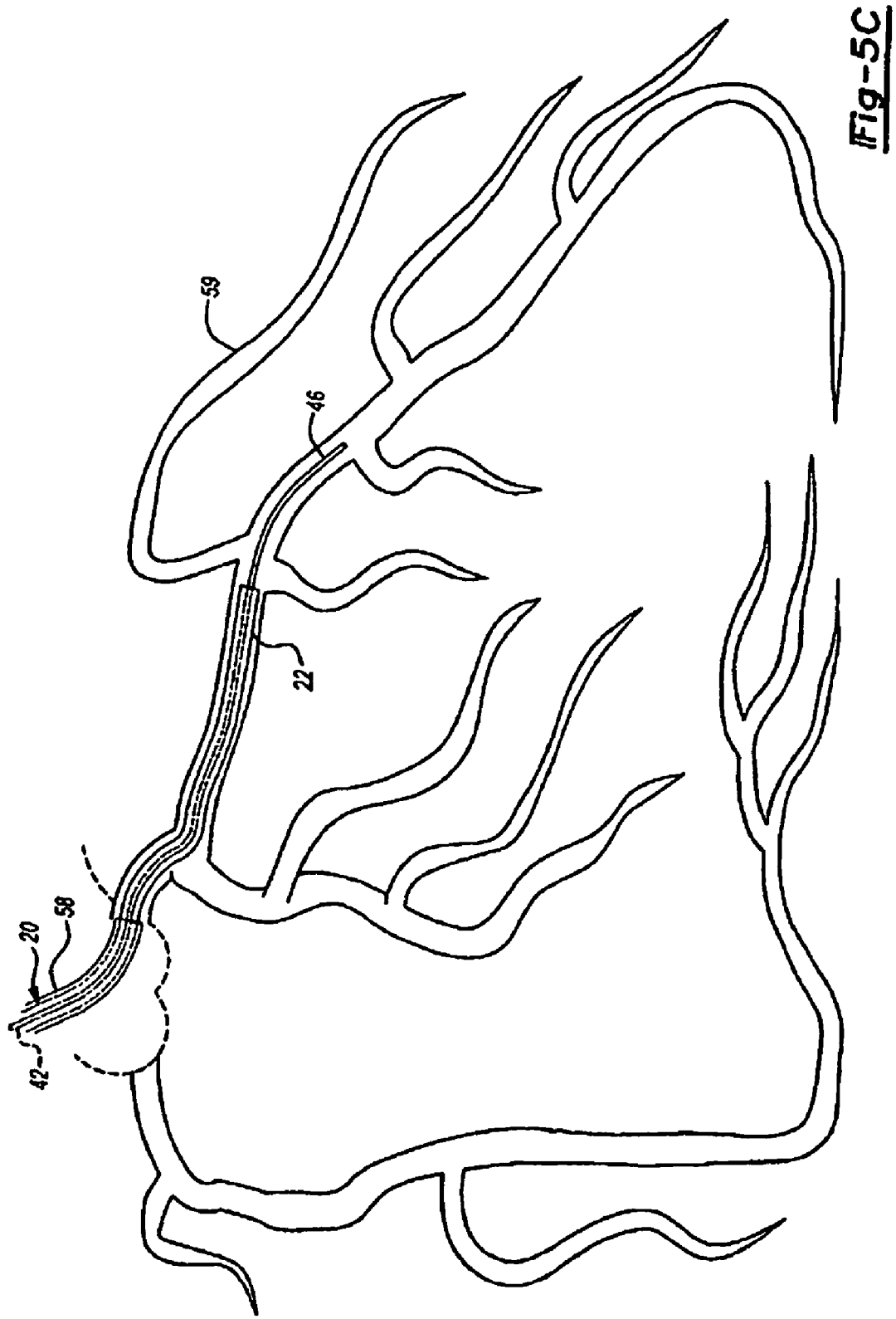

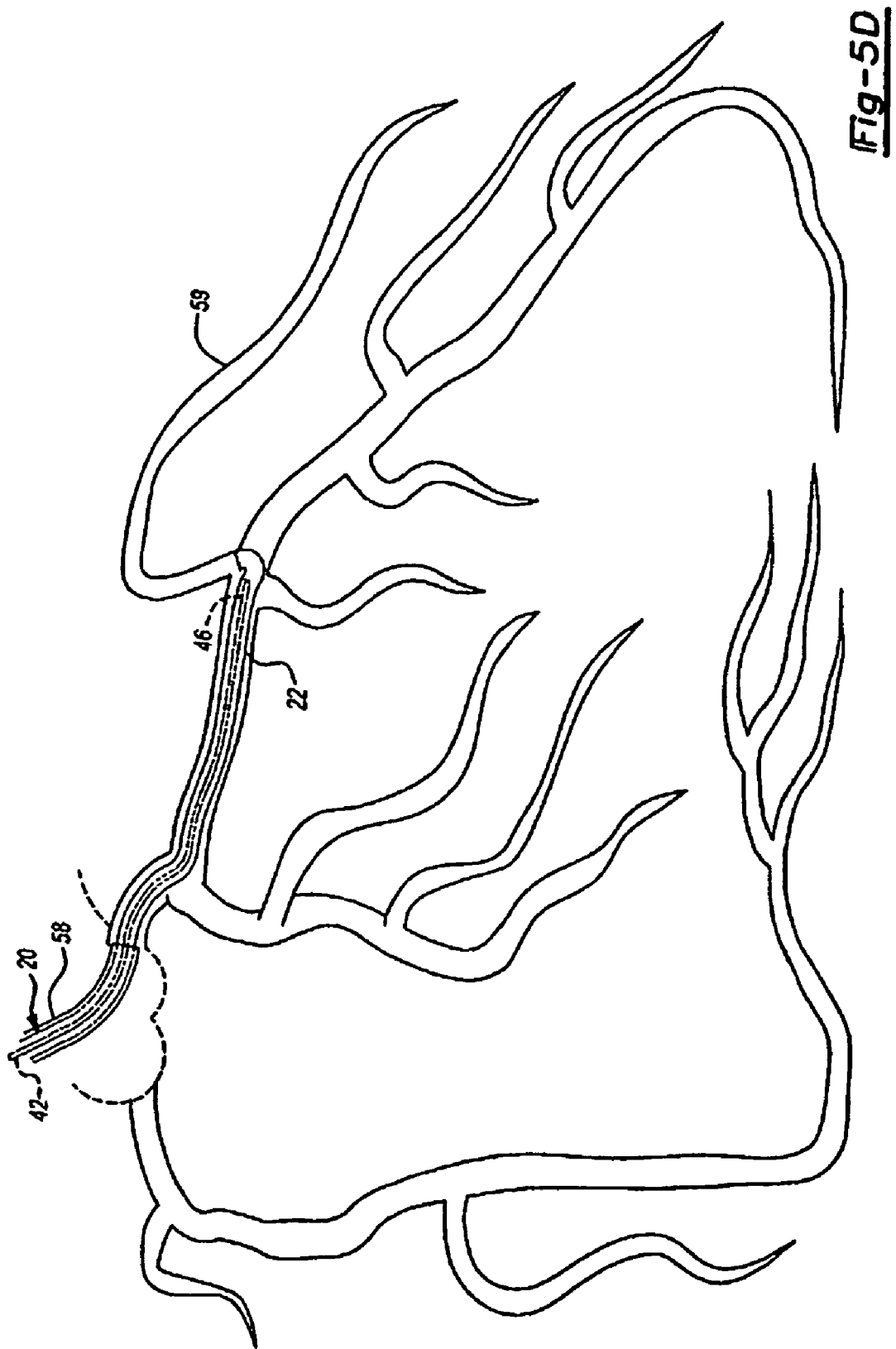

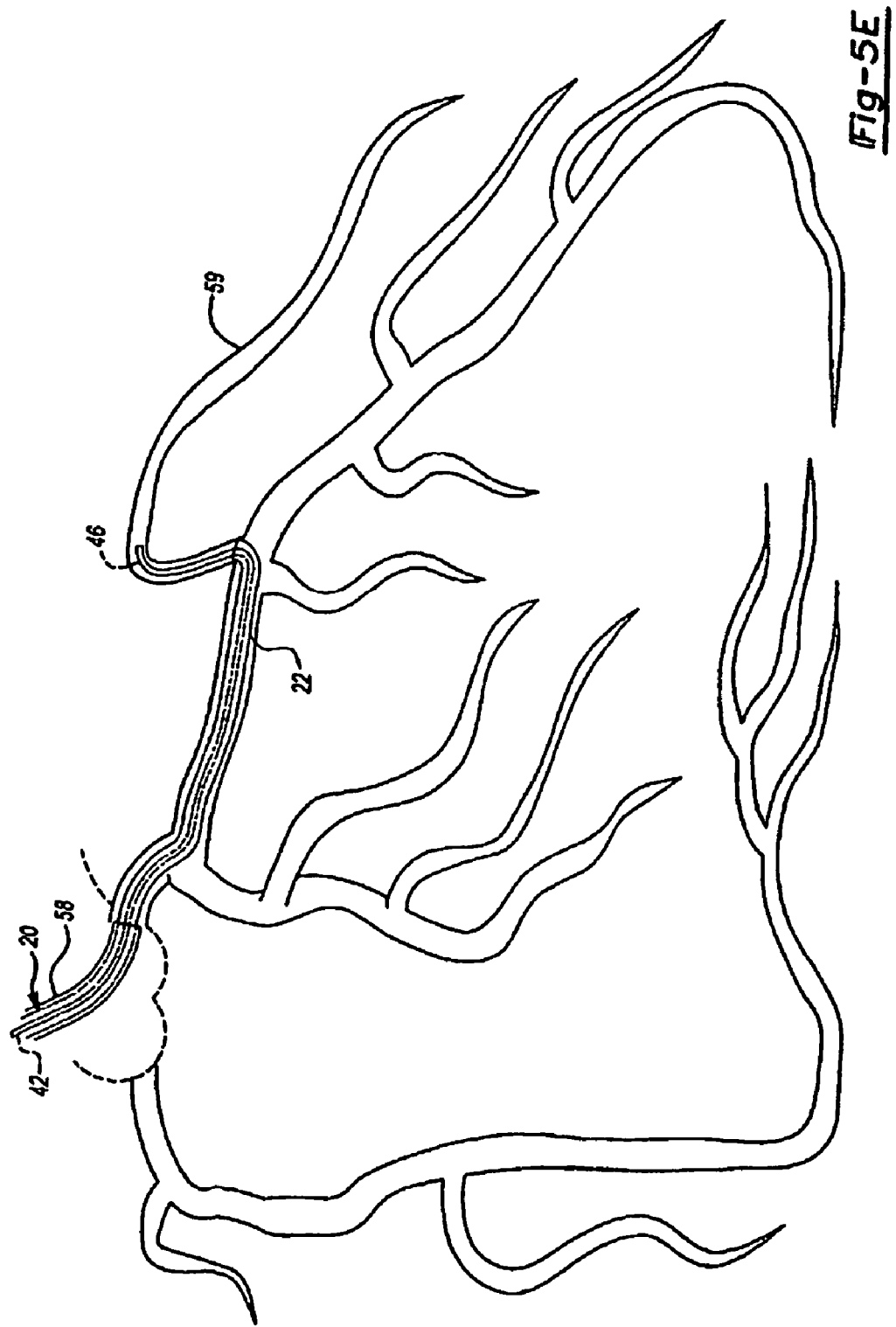

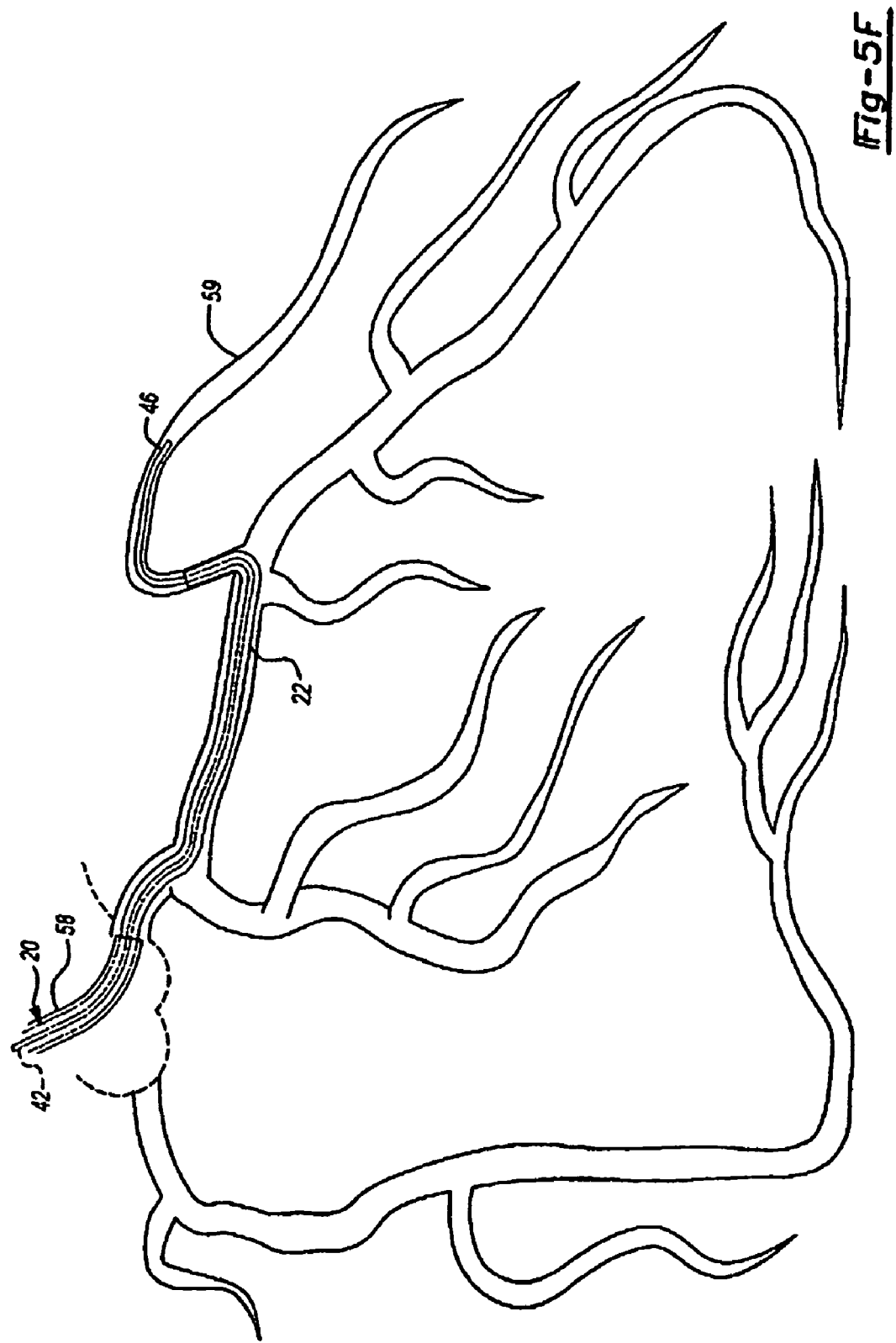

CATHETER WITH FLEXIBLE TIP AND SHAPE RETENTION

CROSS-REFERENCE TO RELATED APPLICATIONS

This application is a continuation of U.S. application Ser. No. 10/064,498, filed on Jul. 22, 2002, now U.S. Pat. No. 7,115,134, and entitled "Catheter with Flexible Tip and Shape Retention".

FIELD OF INVENTION

The present invention is a catheter with a flexible tip and shape retention and a method to guide the catheter through small body passages such as coronary arteries including those at acute angles.

BACKGROUND OF INVENTION

Catheters, known in the art, are slender and flexible tubes inserted into a body cavity or passage to distend or maintain an internal passageway. The catheter can withdraw or introduce fluids or Insert medical devices such as a cardiac stent. Often, small distal branched body passages need to be catheterized. Such catheterizations may require negotiating the catheter through multiple compound curves of varied angles, including acute angles, through these several branchings. In this instance, an acute angle arises when the body branchings require the catheter to make a turn of greater than ninety degrees.

There are catheters known in the art designed to reach specific types of body cavities or passages. For example, a cardiac catheter is a long, fine catheter designed for passage, usually through small peripheral blood vessels and into the chambers of the heart under radiological control. Such catheters are often guided with assistance from a guidewire. A guidewire is a thin, usually flexible, wire that can be inserted into selected body cavities or passages to act as a guide for subsequent insertion of a stiffer or bulkier device, such as a catheter, balloon catheter or stent catheter.

Other catheters and guidewires can include bending or flexing tip members or other attached mechanisms to guide a catheter through branching passages of a body. For example, U.S. Pat. No. 5,401,258 to Voda describes a cardiovascular catheter having a straight proximal end and a bent distal end. U.S. Pat. No. 5,885,259 to Berg describes a catheter having a straight portion followed distally by a primary curved portion. U.S. Pat. No. 6,106,488 to Fleming et al. describes a guidewire having sections of varying stiffness. U.S. Pat. No. 4,020,829 to Wilson et al. describes a guidewire that passes through the lumen of a catheter. The guidewire and catheter are used together to guide the catheter to a desired location in the body passage. The guidewire can provide reinforcement for the thin wall of the catheter. Without this reinforcement, some catheters alone might simply wrinkle or fold back on itself.

Although guidewires and catheters with flexible tips are known in the art, there is a need for a catheter that can be used to catheterize small distal branch passages and can negotiate compound curves of varied angles, including greater than ninety degrees (acute angles in relation to the proximal artery), through several branchings. For example, angle passages greater than ninety degrees occur in fifteen to twenty-five percent of patients requiring angioplasty. To perform an angioplasty (i.e., using a balloon to open a blocked artery) of the coronary arteries or other such blood vessel in the body, a guidewire must first be positioned across the blockage to guide the advancement of the balloon. There are some arteries that arise at a very acute angle from the main artery making it impossible using current technology to position the guidewire in that branch. Further, small catheters known in the art have problems with torque, whip, and windup. Torque is a function of a braid configuration, diameter of the catheter and the flexibility of the materials used. Small catheters have torque problems due to this smaller diameter. Whip is usually caused by windup during torquing of the catheter. As torque builds, the catheter ultimately rotates, causing the stored energy to be released (i.e., whipped) often in unexpected and undesired amounts. Also whip occurs if the materials used are too stiff, especially in a bend area such as the aortic arch.

Although attempts have been made to alter the degree of curvature of a catheter's distal tip, they often require the use of additional or complicated features. These features often require more device manipulation time, thus increasing procedure time, patient discomfort, and increasing the patient's and physician's radiation dosage. Further, more "mechanized" devices increase the likelihood of device malfunction. Therefore, there is a desire and a need to provide a simple catheter having a soft, flexible, pre-formed distal tip that when used in combination with commercially available guidewires of variable stiffness results In the ability to control the direction and angle of advancement of the catheter. Such a device would allow catheterization of body passages, including those that arise at acute angles.

SUMMARY OF INVENTION

Accordingly, the present invention is a catheter small enough to fit within the arteries of a human heart, having a soft flexible pre-formed distal tip with a curvature of ninety degrees or greater, that when used in combination with a variable stiffness guidewire, allows the adjustment of the distal end of the guidewire to be aimed at, and directed into, the branches of a blood vessel. The catheter tip must be flexible enough to allow it to be straightened by a stiff portion of the guidewire, yet have shape retention memory to return to its original curvature of ninety degrees or greater even when a soft portion or no portion of the guidewire is present within the lumen of the catheter.

The present invention catheter can direct a guidewire by combining the plural forces of the variable stiffness guidewire and the catheter's pre-formed distal tip. The catheter can control the radius of curvature of the catheter's distal tip, up to and beyond, ninety degrees of curvature.

The present invention offers a simpler design, leading to reduced device manipulation time. This reduction in time decreases patient discomfort and the patient's and physician's radiation dosage. The present invention's simple design reduces the likelihood of device malfunction.

Specifically, the catheter in one embodiment is about 120 cm in length and designed for use in combination with a variable stiffness guidewire. The catheter has a longitudinal axis, a proximal section and a distal section. The distal section has a soft flexible pre-formed tip having a curvature of ninety degrees or greater and shape retention properties (ability to retain curved shape). The catheter has an inner wall that defines a lumen that runs along the longitudinal axis forming a single continuous tube, a reinforcement braid disposed over said inner wall, the braid being doubled over the proximal two-thirds of the catheter, an outside covering disposed over said reinforcement braid, and said catheter proximal end may further comprise a spacer, disposed between said wall liner and said reinforcement braid. In an alternate embodiment, the catheter can add a steering handle attached to a proximal end of the proximal section.

The catheter dimensions can be sized to function within vascular passages even as small as 2 to 4 mm in diameter. The catheter can include an inner wall of 0.003 cm (0.001 inches) made from a fluorothermoplastic (such as PTFE), nylon, braided nylon, polyurethane, silicone, polyvinyl chloride (PVC), Teflon, polyamid, polyester, elastomer, PET, thermoplastic, hydrocoat, metal, braided metal (such as Nitinol), or other material creating a lumen that is 0.043 cm (0.017 inches) in diameter running along the catheter's longitudinal axis. Marker bands can be added to the catheter's distal end that can be 0.5 to 1.0 mm (0.019 to 0.039 inches) wide. The braid can be braided nylon or metal braid. The catheter's outside covering can be radiopaque and made of Pebax, nylon, braided nylon, polyurethane, silicone, PVC, Teflon, polyamid, polyester, elastomer, PET, thermoplastic, hydrocoat, metal, braided metal (such as Nitinol), or other material and thick enough to give said distal section of said catheter an outside diameter of 0.074 cm (0.029 inches). The spacer can be made of nylon, braided nylon, polyurethane, silicone, PVC, Teflon, polyamid, polyester, elastomer, PET, thermoplastic, hydrocoat, metal, braided metal (such as Nitinol), or other material and thick enough to give an overall proximal section catheter diameter of 0.132 cm (0.052 inches).

The catheter distal section pre-formed tip comprises a straight subsection, followed distally by a pre-formed curved subsection, followed distally by a second straight subsection. The pre-formed curved subsection has a curve of ninety degrees or greater, and typically the curve is 180 degrees. The stiffness of the pre-formed tip varies by section. For example, the stiffness of the straight subsections are greater than the stiffness of the curved subsection.

Using the present invention, body passages can be catheterized by introducing the guidewire followed by the catheter and advancing the catheter and guidewire concentrically until reaching the first branched passageway. The guidewire can then be withdrawn into the catheter allowing the catheter's distal tip to resume its pre-formed angle of curvature. By rotating the catheter, the distal tip can be directed to the origin of the first branched passageway. The guidewire can then be advanced and using the plurality of forces the desired angle of curvature of the distal tip of the catheter can be created, thereby allowing the guidewire to be advanced into the first branched passageway. Successively branched passageways can be cannulated by cooperatively manipulating and slidably adjusting the relative position of the guidewire and catheter from the exterior of the body until the desired body passageway is reached.

Other features of the present invention will become more apparent to persons having ordinary skill in the art to which the present invention pertains from the following description taken in conjunction with the accompanying figures.

BRIEF DESCRIPTION OF DRAWINGS

The foregoing advantages and features, as well as other advantages and features, will become apparent with reference to the description and figures below, in which like numerals represent like elements, and in which:

FIGS. 5A-5F are schematic views of a typical arterial system such as a coronary artery tree showing successive steps in the use of the present invention, showing advancement of a catheter having a soft flexible pre-formed distal tip and a variable stiffness guidewire, turning into several branches including one at an acute angle.

DETAILED DESCRIPTION

The present invention is a catheter with a flexible tip and shape retention and a method to guide the catheter through small body passages such as coronary arteries including those at acute angles. The present catheter is small enough to fit within the arteries of a human heart, having a soft flexible pre-formed distal tip with a curvature of ninety degrees or greater, that when used in combination with a variable stiffness guidewire, allows the adjustment of the distal end of the guidewire to be aimed at and directed into the branches of a blood vessel. The catheter tip must be flexible enough to allow it to be straightened by the stiff portion of the guidewire, yet have shape retention memory to return to its original curvature of ninety degrees or greater even when a soft portion of the guidewire is present within the lumen of the catheter. In general, the present invention catheter can direct a guidewire by combining the plural forces of a variable stiffness guidewire and the catheter's pre-formed distal tip. The catheter can control the radius of curvature of the catheter's distal tip up to and beyond ninety degrees of curvature.

The present invention offers a simpler design, leading to reduced device manipulation time. This reduction in time decreases patient discomfort and the patient's and physician's radiation dosage. The present invention's simple design reduces the likelihood of device malfunction.

Figure 1:
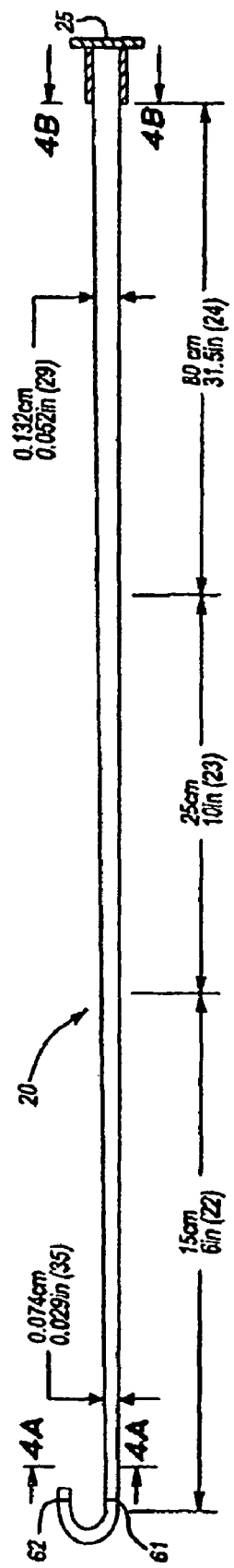
FIG. 1 is a planar view of a catheter of the present invention having a soft flexible pre-formed distal tip with shape retention.

FIG. 1 is a planar view of one embodiment of a catheter of the present invention having a soft flexible pre-formed distal tip and is generally referred to at 20. In general, the catheter 20 dimensions can be sized to function within vascular passages, such as a coronary tree, even as small as 2 to 4 mm in diameter. The catheter 20, can have a distal section 22, an intermediate section 23, and a proximal section 24. It can be noted that the invention can be practiced without the intermediate section 23 just making the proximal section 24 longer to maintain the same overall length of about 120 cm (47.24 inches). A catheter steering handle 25, known in the art, can be mounted at a proximal end of the proximal section 24. The materials used in the intermediate section 23 can be softer than the proximal section 24 to reduce whip and windup, such as in the aortic arch area. The materials used in the distal section 22 can be slightly softer than the intermediate section 24, again in an effort to reduce whip and windup while in use. The catheter 20 can be constructed of any material known in the art suitable for constructing catheters to catheterize body passages, such as: braided nylon, Nitinol, metal braid, polyurethane, other suitable polyamide materials such as copolyamides (including polyether block amides such as Pebax available from Elf Atochem), and polytetrafluoroethylene (PTFE) (a fluorothermoplastic).

The length and diameter of the proximal section 24 will depend on the application for which the catheter 20 is being used. In the embodiment illustrated, the proximal section 24 is approximately 80 centimeters (cm) (31.5 inches) long and has an outer diameter of approximately 0.132 cm (0.052 inches)(shown at 29). The intermediate section 23 can be approximately 25 cm (10 inches). The distal section can be approximately 15 cm (6 inches) and have an outer diameter of approximately 0.074 cm (0.029 inches) (shown at 35).

Figure 4A:
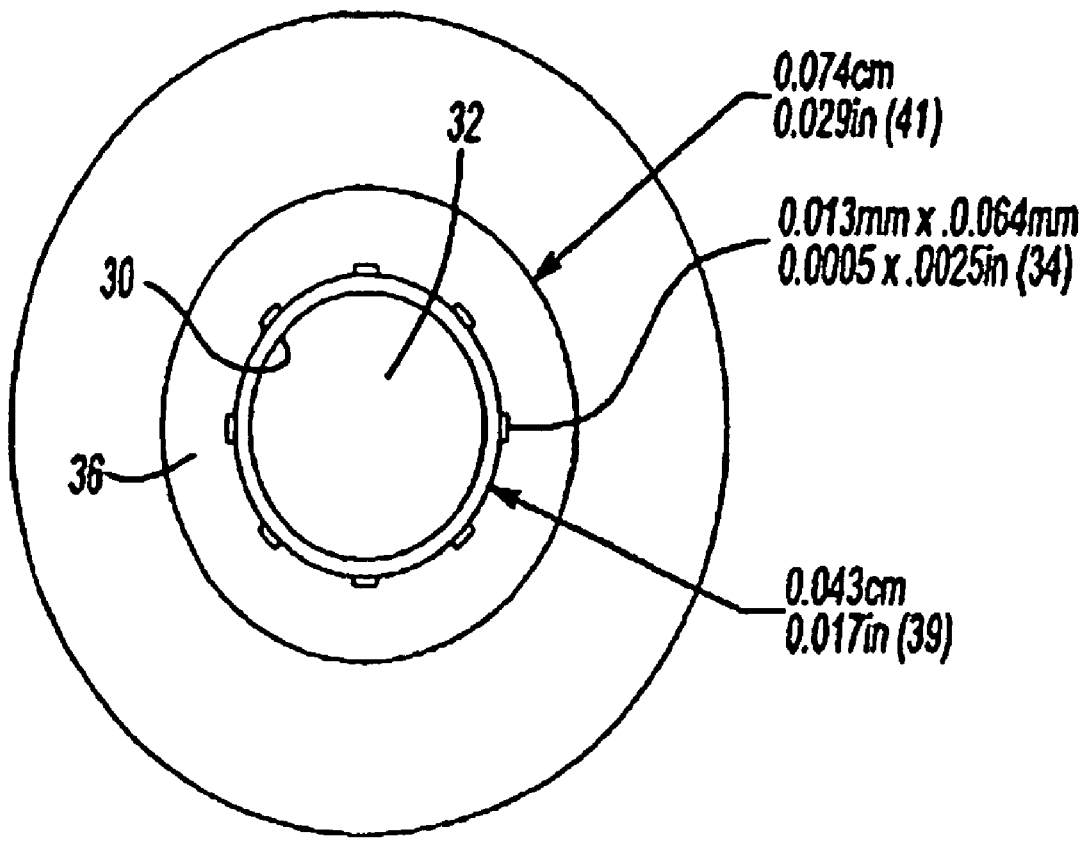
FIGS. 4A and 4B are cross sectional end views of the catheter of the present invention as indicated in FIG. 1 from the distal end facing the proximal end, and from the proximal end facing the distal end, respectively.
Figure 4B:
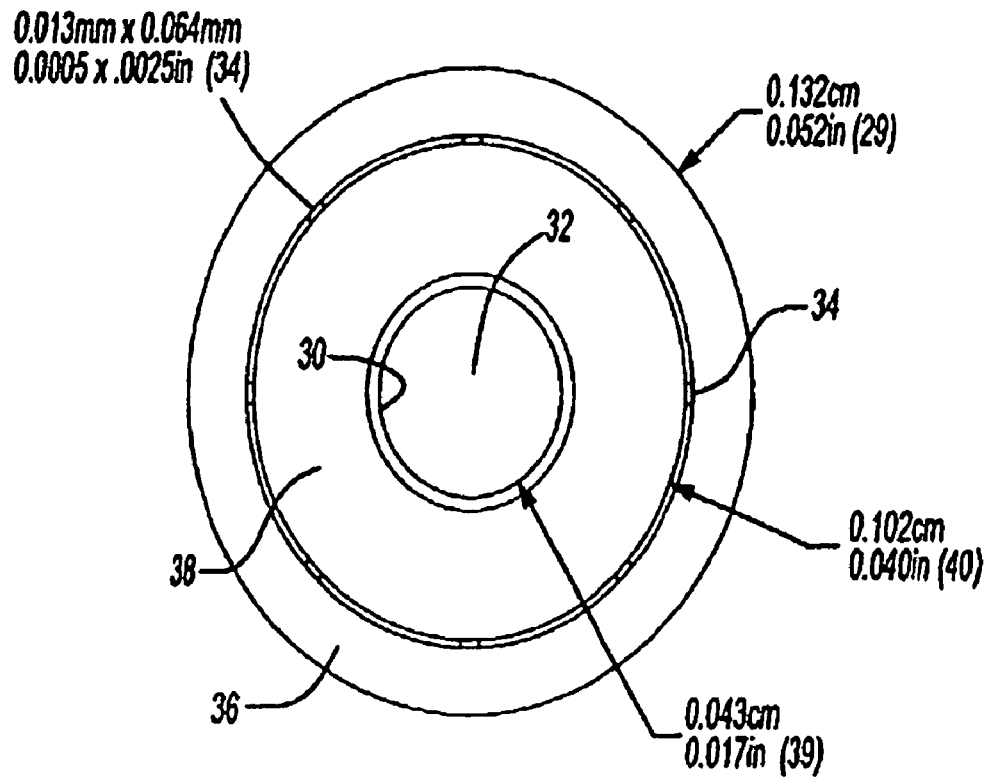

FIGS. 4A and 4B illustrate cross sections of the catheter of the present invention as indicated in FIG. 1 from the distal section 22 end facing the proximal section 24 end and from the proximal section 24 end facing the distal section 22 end, respectively. FIG. 4A shows the distal section 22 has an inner wall, such as a wall liner 30, that defines a lumen 32 of the catheter 20 along a longitudinal axis of the catheter 20 forming a single continuous tube. The wall liner 30 can be approximately 0.003 cm (0.001 inches) thick and made from a fluorothermoplastic such as PTFE. The lumen can be approximately 0.043 cm (0.017 inches) in diameter (shown at 39). A braid 34 for reinforcement is disposed over the wall liner 30. The braid 34 can be braided nylon or metal braid and can be approximately 0.013 mm×0.064 mm (0.0005×0.0025 inches). The braid 34 in this embodiment is a stainless steel high tensile wire with a high density and runs the length of the catheter 20. The proximal two-thirds of the catheter 20 can have a double braid (braid over braid) and has a slightly larger diameter than the distal section as shown at 34 in FIG. 4B. This double braid and wire configuration allows for greater transmission of torque, thus reducing whip and windup. A soft outside covering 36 is added and disposed over the braid 34. The soft outside covering 36 in one embodiment is a combination of a Pebax 3533 radiopaque and Pebax 5533/3533 blend radiopaque. The outside covering 36 can also be made of nylon, braided nylon, polyurethane, silicone, PVC, Teflon, polyamid, polyester, elastomer, PET, thermoplastic, hydrocoat, metal, braided metal (such as Nitinol), or other material and can be thick enough to give the distal section 22 an overall distal tip outside diameter of approximately 0.074 cm (0.029 inches) (shown at 41) and an overall diameter of the proximately two-thirds of the catheter of approximately 0.132 cm (0.052 inches).

FIG. 4B illustrates a cross section of the catheter 20 of the present invention as indicated in FIG. 1 from the proximal section 24 end facing the distal section 22 end. As indicated, a spacer 38 can be added beginning at the intermediate section 23 and disposed between the wall liner 30 and the braid 34 and throughout the entire intermediate section 23 and proximal section 24. The spacer can be made of Pebax, nylon, braided nylon, polyurethane, silicone, PVC, Teflon, polyamid, polyester, elastomer, pet, thermoplastic, hydrocoat, metal, braided metal (such as Nitinol), or other material. The spacer 38, at the cross section as indicated in FIG. 4B, adds approximately 0.058 cm (0.023 inches) to the outside diameter of catheter 20, for a total catheter 20 proximal section diameter of 0.132 cm (0.052 inches) (shown at 29), and a proximal section braid diameter of approximately 0.103 cm (0.040 inches) (shown at 40).

Figure 1A:
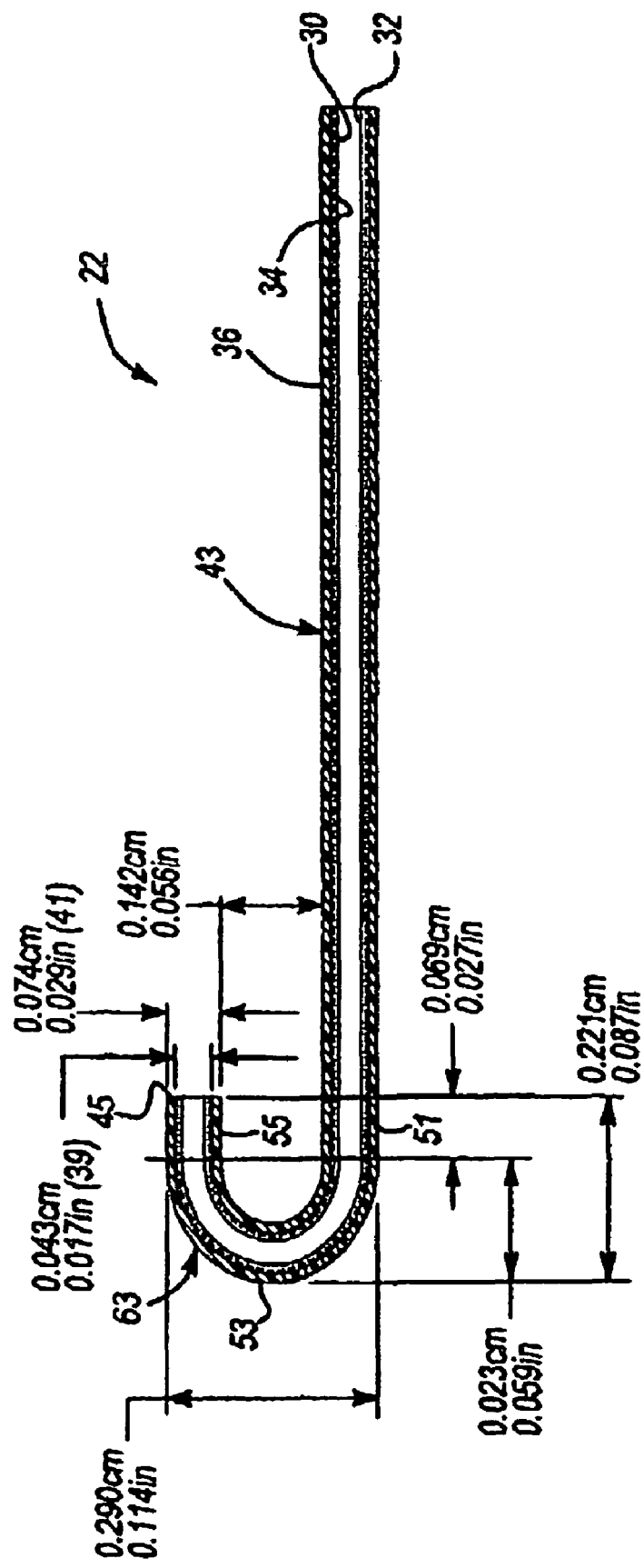
FIG. 1A is a close-up view of the distal section of a catheter of the present invention.

The distal section 22 is shown in close up in FIG. 1A and illustrates an important feature of the present invention, a pre-formed distal tip 63 having shape retention. The distal section 22 has a distal section proximal end 43 and a distal section tip 45. The distal section proximal end 43 of the distal section 22 is fixedly attached to the intermediate section 23 of the catheter 20. The pre-formed distal tip section 63 can have a plurality of subsections, comprising at least one straight subsection and at least one subsection having a pre-formed curvature. Many types of curvatures are possible. The distal section 22 can be constructed of any material suitable and known in the art such as a spring, nylon, braided nylon, polyurethane, or other polymer, braided metal (such as Nitinol). The material must allow the tip to be flexible and provide shape retention.

In the illustrated embodiment, the pre-formed distal tip 63 comprises a first straight subsection 51; followed distally by a pre-formed curved subsection 53; followed distally by an optional second straight subsection 55. The bending stiffness of the various subsections can vary. For example, the bending stiffness of the first straight subsection 51 can be greater than a bending stiffness of the pre-formed curved subsection 53 and the bending stiffness of the second straight subsection 55 can greater than a bending stiffness of the pre-formed curved subsection 53. The amount of curvature of the pre-formed distal tip 63 can be controlled by a variable stiffness guidewire. The pre-formed distal tip 63 can be formed of, for example, fused nylon plastic, or polyurethane. In an alternate embodiment, the pre-formed distal tip 63 can further include a wire having shape memory characteristics or braided metal.

The pre-formed distal tip 63 of this embodiment can have distal marker bands 61 and 62 to define the beginning and end of the pre-formed curved subsection 53. The marker bands can be made from platinum and can be 0.5 to 1.0 mm (0.019 to 0.039 inches) wide. The marker bands allow the pre-formed distal tip 63 to be visualized under x-ray, allowing the direction of the pre-formed distal tip 63 to be determined. This can assist in guiding the pre-formed distal tip 63 of the catheter 20 to the branch passage to be cannulated.

In the illustrated embodiment, the first straight subsection 51 can be approximately 0.069 cm (0.027 inches) long and can have an outer diameter of approximately 0.274 cm (0.029 inches). The pre-formed curved subsection 53 can be approximately 0.290 cm (0.059 inches) long, and has, by way of example only, an outer diameter of approximately 0.274 cm (0.029 inches), and curves to form a 180-degree angle having a radius of curvature of approximately 0.023 cm (0.059 inches). The second straight subsection 55 can be approximately 0.069 cm (0.027 inches) long and can have an outer diameter of approximately 0.047 cm (0.029 inches). The overall dimension of the outside diameter of the pre-formed distal tip 63 can be approximately 0.074 cm (0.114 inches).

As stated previously, passing through the longitudinal axis of the catheter 20 is the single lumen 32. The lumen 32 is designed to slidably receive a commercially available variable stiffness guidewire. In the illustrated embodiment, the lumen 32 can have a diameter of approximately 0.043 cm (0.017 inches)(shown at 39).

Figure 2:
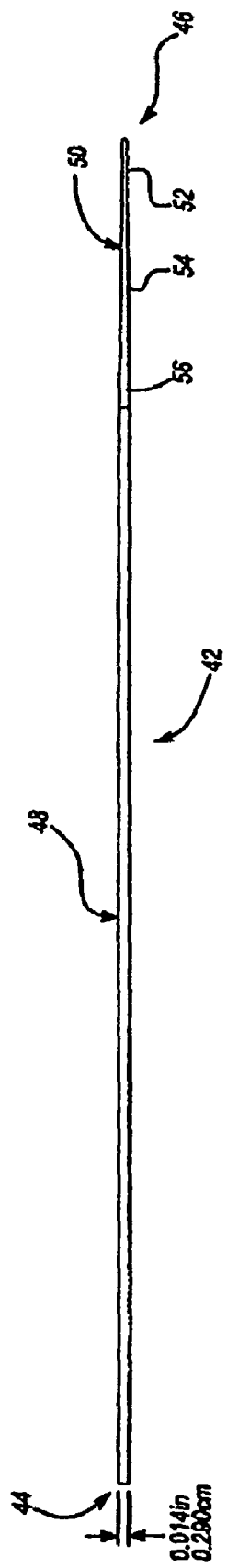
FIG. 2 is a planar view of a prior art, variable stiffness guidewire.

FIG. 2 shows a commercially available variable stiffness guidewire 42. The guidewire 42 has a guidewire proximal end 44 and a guidewire distal end 46. The guidewire 42 also has a body section 48 and a variable stiffness distal tip section 50. The bending stiffness of the variable stiffness distal tip section 50 increases moving from the guidewire distal end 46 toward the guidewire proximal end 44. For demonstration purposes, three points, 52, 54, and 56, are labeled along the variable stiffness distal tip section 50. The bending stiffness of the variable stiffness distal tip section 50 is greater at point 56 than at points 54 and 52; and the bending stiffness is greater at point 54 than at point 52. In the illustrated embodiment, the guidewire can have a diameter of approximately 0.290 cm (0.014 inches) and can be 180 to 300 cm (70.87 to 117.00 inches) long.

A combination of the catheter 20 with a pre-formed distal tip 63 and the guidewire 42 is illustrated in FIGS. 3A-D. As the guidewire 42 passes through the distal section 22, the guidewire 42 acts to straighten the pre-formed curve subsection 53 of the pre-formed distal tip 63. The extent to which the pre-formed curved subsection 53 is straightened depends on the relative stiffness of the pre-formed curved subsection 53 of the pre-formed distal tip 63 and the guidewire 42. Varying the position of the guidewire 42 within the catheter 20 can control the amount of curvature. More specifically, the amount of curvature of the pre-formed curve subsection 53 of the pre-formed distal tip 63 of the catheter 20 can be controlled by varying the position of the variable stiffness distal tip section 50 of the guidewire 42 within the pre-formed curve subsection 53.

Figure 3A:
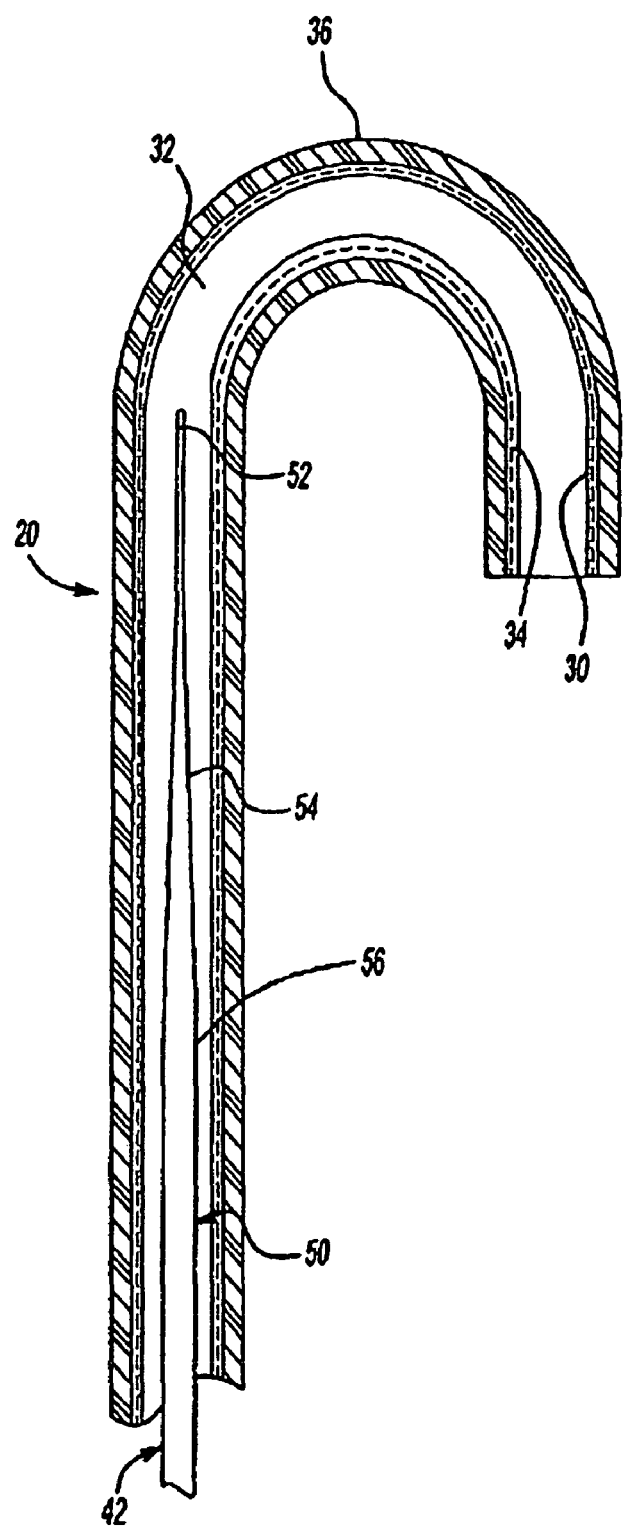
FIGS. 3A-3D are planar views of a prior art variable stiffness guidewire inserted within the lumen of the catheter of the present invention.

FIG. 3A shows a guidewire 42 slidably inserted into the catheter 20. Point 52 of the variable stiffness distal tip section 50 of the guidewire 42 is approximately aligned with the first straight subsection 51 of the pre-formed distal tip 63 of the catheter 20. In this instance, the guidewire 42 is exerting no straightening force on the pre-formed curved subsection 53 and the catheter 20 retains its original shape.

Figure 3B:
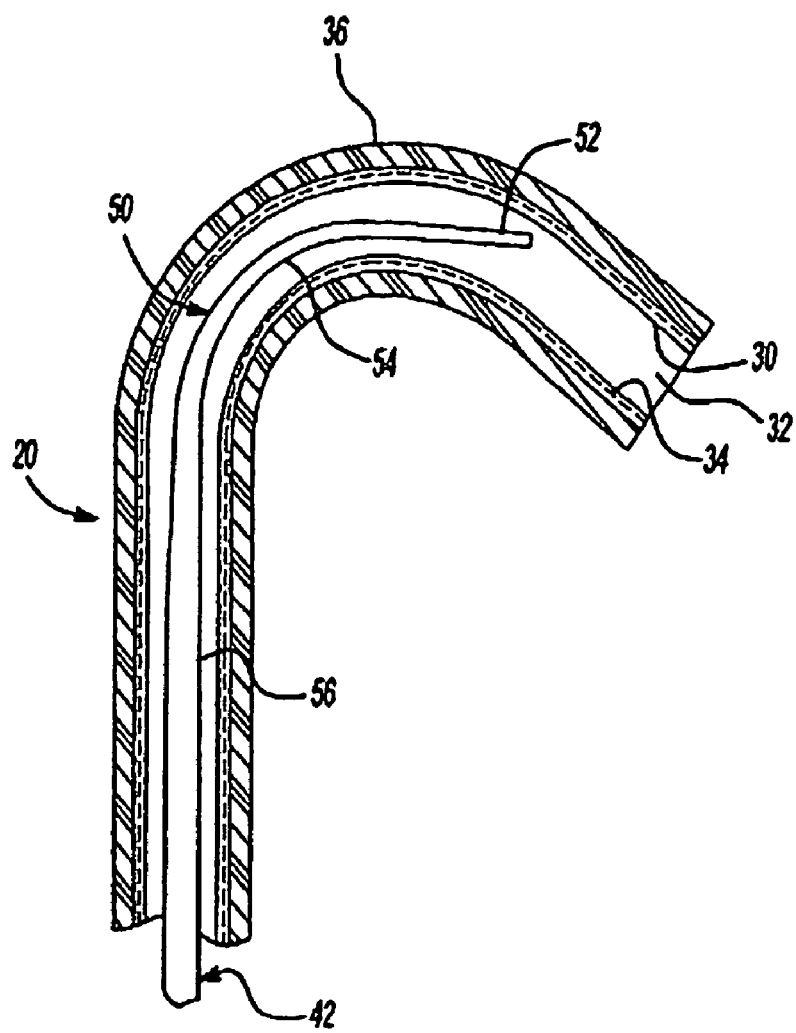

FIG. 3B shows the guidewire 42 slidably advanced through the catheter 20 such that point 52 of the variable stiffness distal tip section 50 of the guidewire 42 is approximately aligned with pre-formed curved subsection 53 of the pre-formed distal tip 53 of the catheter 20. Note that the pre-formed curved subsection 63 has been straightened slightly. This straightening is caused by the guidewire 42 imparting a straightening force on the pre-formed curved subsection 53.

Figure 3C:
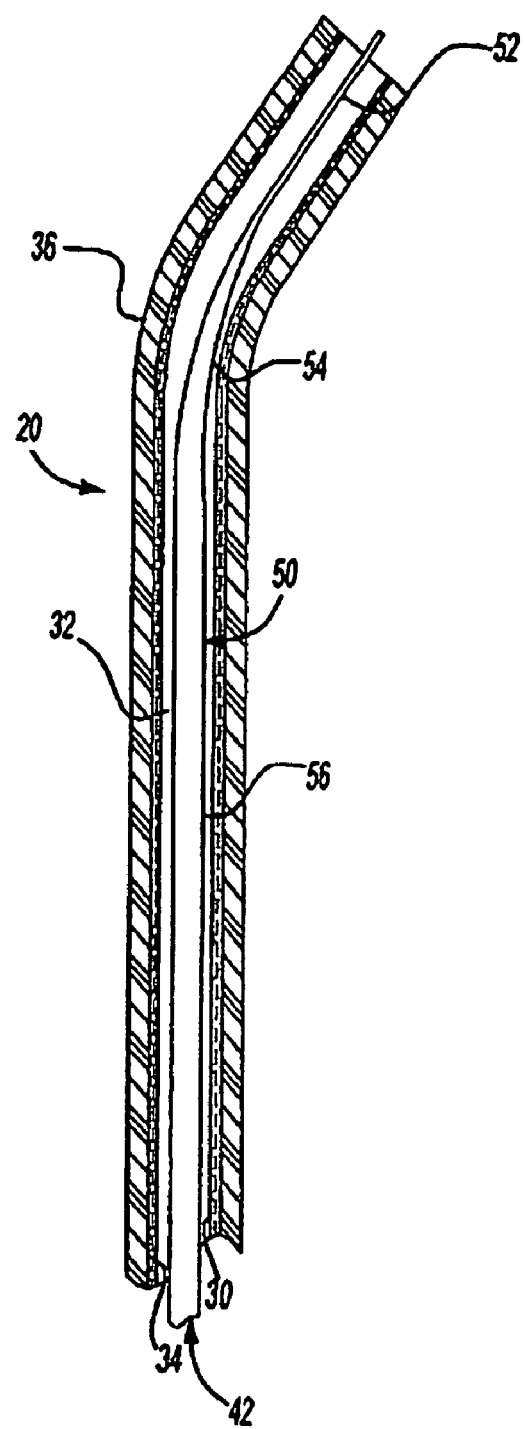

FIG. 3C shows the guidewire 42 further advanced through the catheter 20 such that point 54 of the variable stiffness distal tip section 50 of the guidewire 42 now engages the pre-formed curved subsection 53 of the pre-formed distal tip 63. The guidewire 42 imparts a greater straightening force on the pre-formed curved subsection 53 and results in less curvature in subsection 53.

Figure 3D:
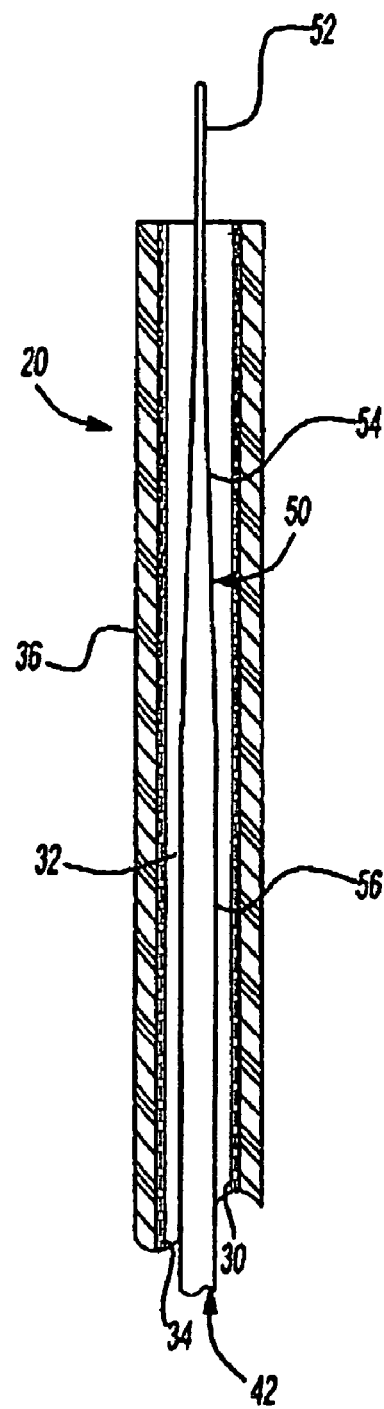

FIG. 3D shows the guidewire 42 further advanced through the catheter 20 such that point 56 of the variable stiffness distal tip section 50 of the guidewire 42 now engages the pre-formed curved subsection 53 of the pre-formed distal tip 63. The guidewire 42 imparts an even greater straightening force that results in the pre-formed curved subsection 53 becoming substantially straight.

FIGS. 5A-5F show how the catheter 20 and a guidewire 42 are used together to guide the catheter 20 to a desired location in a body passage. In this instance, a coronary arterial tree is illustrated. Generally, the method of using the catheter 20 of the present invention within a coronary arterial tree involves introducing the guidewire 42 followed by the catheter 20 and advancing the catheter 20 and guidewire 42 concentrically until reaching the first branched passageway. The guidewire 42 can then be withdrawn into the catheter 20 allowing the catheter's pre-formed distal tip 63 to resume its pre-formed angle of curvature. By rotating the catheter 20 the pre-formed distal tip 63 can be directed to the origin of the first branched passageway. The guidewire 42 can then be advanced and using the plurality of forces the desired angle of curvature of the pre-formed distal tip 63 of the catheter 20 can be created, thereby allowing the guidewire 42 to be advanced into the first branched passageway. Successively branched passageways can be cannulated by cooperatively manipulating and slidably adjusting the relative position of the guidewire 42 and catheter 20 from the exterior of the body until the desired body passageway is reached and performing the desired diagnostic or therapeutic procedure.

Specifically, the example illustrated in FIGS. 5A-5F involves a technique using the catheter 20 of the present invention in a femoral-coronary angiogram procedure. Entry into an arterial stream is made by a hollow needle puncture through the skin in the groin (not shown) into a femoral artery in a procedure well known in the art. The distal portion of a prior art guidewire is advanced into the femoral artery through the needle and the needle is removed. This leaves the guidewire with a distal end extending into the femoral arterial lumen with a proximal end extending outside the skin. Next, a sheath (such as a 12 cm long, hollow plastic tube with a hemostatic valve on the end of approximately 2 mm diameter) is placed over the prior art guidewire and is inserted into the femoral artery. This guidewire is withdrawn and the sheath is left in place in the femoral artery with the hemostatic valve left outside the body.

Figure 5A:
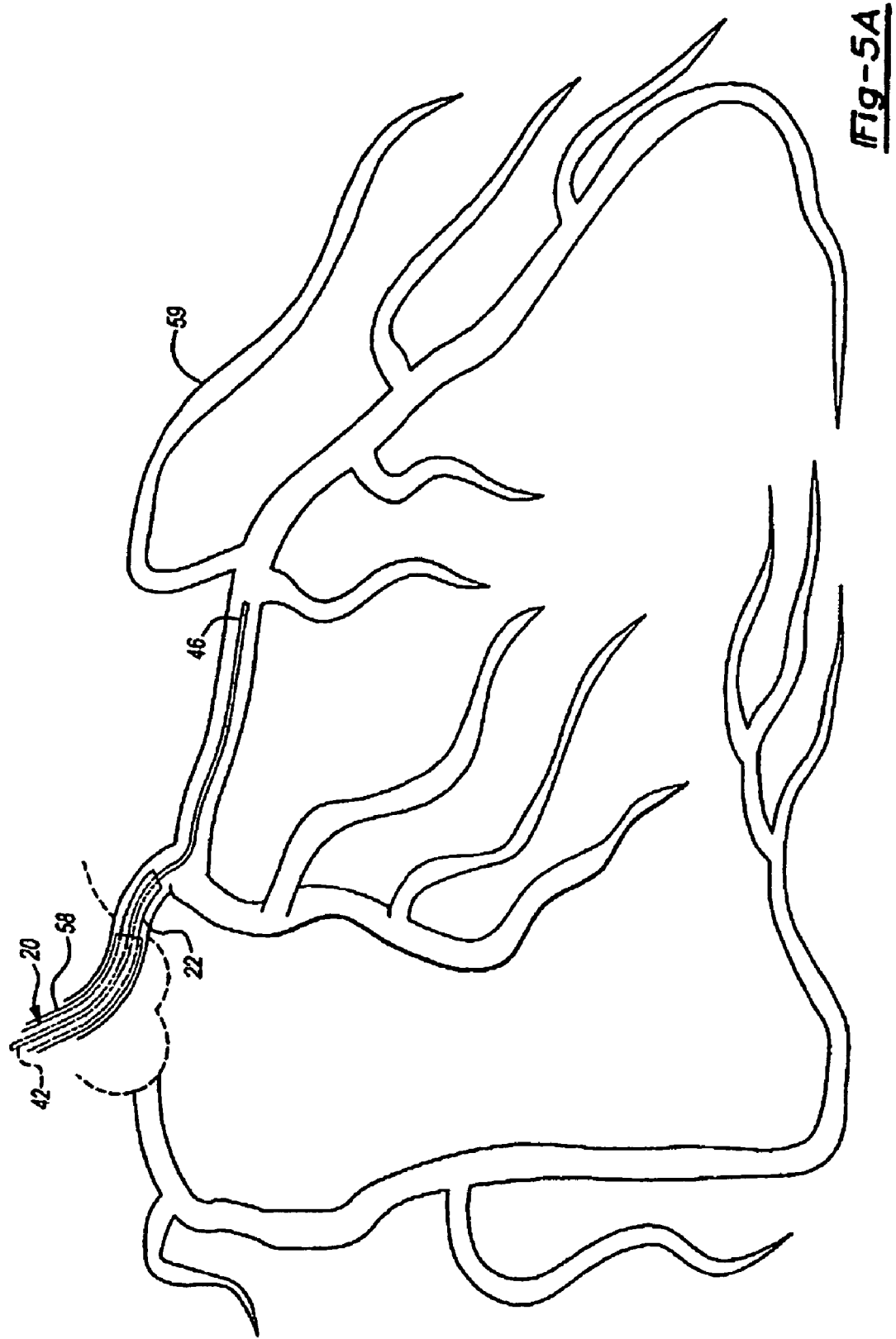

The prior art guiding catheter 58 is then inserted through the hemostatic valve of the sheath and is advanced to and positioned in the ostium of one of the coronary arteries or vein grafts such as shown in FIG. 5A. Next the small 0.290 cm (0.014 inches) guidewire 42 is inserted into the guiding catheter and advanced into the coronary artery.

The next step is to introduce the distal section 22 of the catheter 20 of the present invention such as shown in FIG. 1, by pushing it over the projecting end of the guidewire 42, into the sheath in the femoral artery up the guiding catheter 58 in the aorta to the coronary artery to the position shown in FIG. 5A. When the catheter 20 is placed on the guidewire 42 extending through the sheath outside the body, the catheter 20 is positioned relative to the guidewire 42, such that the pre-formed curved subsection 53 of the pre-formed distal tip 63 is straightened.

Once the straightened catheter 20 is advanced to the position near the branch of the coronary artery that is desired to be cannulated (as shown in FIGS. 5A, 5B, and 5C), the guidewire 42 is pulled back into the catheter 20 (as shown in FIG. 5D). The desired coronary artery to be cannulated is the first diagonal shown at 59. In this instance the first diagonal 59 branches at an acute angle.

As shown in FIG. 5D, the stiff portion of the guidewire 42 is pulled back allowing the catheter 20 to resume the original curved-tip configuration. By manually rotating the catheter 20, it can be positioned to point at or enter the desired branch of the coronary artery. Next, as shown in FIG. 5E, the guidewire 42 is advanced into the branch as directed by the curved tip catheter 20. At this point, the catheter 20 can be advanced over the guidewire 42 into the branch artery as shown in FIG. 5F. These steps can be repeated to cannulate subsequent branches of the coronary arterial tree as well.

The final step is to remove the guidewire 42 entirely, leaving the catheter 20 in place, ready for injection of fluid, medications, or other desired diagnostic or therapeutic procedure (such as a angioplasty balloon or stent placement known in the art), with the pre-formed distal tip 63 of the distal section 22 of the catheter 20 disposed in the coronary artery and the proximal section 24 extending out through the skin in the groin. Alternatively, the final step could be to remove the catheter 20 leaving the guidewire 42 in place, allowing for advancement of an angioplasty balloon or stent over the guidewire 42 to the desired location.

The above-described embodiment of the invention is provided purely for purposes of example. Many other variations, modifications, and applications of the invention may be made.

The invention claimed is:

1. A method for steering a guide wire within bodily passages of a patient, the method comprising:
    introducing a variable stiffness guidewire into a first body passage;

targeting a branch body passage having a diameter of not more than 4 mm and extending from the first body passage at an angle;

deploying a guide catheter over the guidewire such that a distal section of the guide catheter is adjacent the branch passage;

manipulating the guide catheter such that a distal tip portion of the distal section forms a curved shape;

manipulating the guidewire and the guide catheter relative to one another to change an effective curvature of the curved shape distal tip portion until a distal end of the distal tip portion faces the branch body passage;

distally advancing the guidewire such that the curved distal tip steers the guidewire into the branch body passage; and advancing the guide catheter over the guidewire and into the branch body passage.

2. The method of claim 1, wherein the distal tip portion has a pre-determined curvature in a natural state, and further wherein the effective curvature is between the pre-determined curvature and a straightened state.

3. The method of claim 1, wherein:

the catheter is generally flexible to conform to vasculature of a body, the catheter extending from a proximal end to a distal end and having an intermediate portion therebetween, the catheter having a pre-formed curved portion in the curved distal tip, the curved portion having a flexibility to permit straightening of the curved distal tip by sliding the guidewire relative to the catheter; and wherein manipulating the catheter to form the curved shape includes:

slidably adjusting the variable stiffness guidewire relative to the catheter and straightening the pre-formed curved portion; and withdrawing the guidewire into the catheter allowing the curved distal tip to resume the pre-formed angle of curvature.

4. The method of claim 3, further comprising the steps of:
rotating the proximal end of the catheter to rotate the distal tip to different orientation, and advancing further the guidewire and catheter.

5. The method of claim 3, further comprising the step of administering medication through the catheter.

6. The method of claim 3, further comprising the steps of removing the catheter and advancing an angioplasty balloon over the guidewire.

7. The method of claim 3, further comprising the steps of removing the catheter and advancing a stent over the guidewire.

8. The method of claim 3, further comprising removing the guidewire.

9. The method of claim 1, wherein the branch body passage is a primary branch body passage, and further wherein after the step of advancing the guide catheter into the primary branch body passage, the method further comprising:

targeting a secondary branch body passage extending from the primary branch body passage at an angle differing from the angle of extension of the primary branch body passage from the first body passage;

deploying the guide catheter over the guide wire within the primary branch body passage such that the distal section of the guide catheter is adjacent the secondary branch body passage;

manipulating the guidewire and the guide catheter relative to one another such that the distal tip portion forms the curved shape;

further manipulating the guide catheter and the guidewire such that the distal end faces the secondary branch body passage;

distally advancing the guidewire such that the curved distal tip steers the guidewire into the secondary branch body passage; and advancing the guide catheter over the guidewire and into the secondary branch body passage.

* * * * *